United States Patent [19]
Bales et al.

[11] Patent Number: 5,258,004
[45] Date of Patent: Nov. 2, 1993

[54] DOUBLE ACTING, DUAL PIVOT THORACOSCOPIC SURGICAL LUNG CLAMPS

[75] Inventors: Thomas O. Bales, Coral Gables, Fla.; Roger L. Hildwein, Loveland, Ohio; Jurgen Kortenbach, Fort Lauderdale, Fla.

[73] Assignees: Symbiosis Corporation; Ethicon, Inc., Miami, Fla.

[21] Appl. No.: 780,016

[22] Filed: Oct. 21, 1991

Related U.S. Application Data

[63] Continuation-in-part of Ser. No. 680,392, Apr. 4, 1991, Pat. No. 5,192,298.

[51] Int. Cl.$^5$ .............................................. A61B 17/00
[52] U.S. Cl. ................................................... 606/205
[58] Field of Search ................................. 606/205–208, 606/167, 170, 176, 157–158; 128/749, 751

[56] References Cited

U.S. PATENT DOCUMENTS

| 3,464,677 | 7/1965 | Springer | 128/751 |
| 3,845,636 | 7/1975 | Schmidt | 606/174 |
| 4,669,471 | 6/1987 | Hayashi | 606/174 |
| 4,950,273 | 8/1990 | Briggs | 606/205 |

OTHER PUBLICATIONS

American V. Mueller, "The Surgical Armamentarium, Instruments, Professional Equipment," 1980, pp. 27, 73, 92, 129, 357.

Sklar Products, "Surgical Instruments, Suction and Pressure Apparatus," 18th Edition, 1973, pp. 100, 192, 311, 329, 349, and 309.

Primary Examiner—Lee S. Cohen
Assistant Examiner—Samuel Gilbert
Attorney, Agent, or Firm—David P. Gordon

[57] ABSTRACT

Lung clamp end effectors for a thoracoscopic surgical instrument are disclosed. The lung clamp end effectors have a base portion, an intermediate portion, and a distal portion. Each base portion has a first through-hole for pivotally engaging a pin of the clevis of the thoracoscopic surgical instrument, and preferably, a second through-hole used in conjunction with connecting links which connect the lung clamp end effector to the push rod. The through-holes on a particular end effector are located on opposite sides of the longitudinal axis of the tool, thereby providing strong clamping action. The lung clamps are further arranged with their distal portions increasing in width to approximately 10 mm as they extend distally. The distal portion also have cut-outs which increase in width as they extend distally. The lung clamp end effectors are at least two inches long from their respective pivot through-holes to their respective distal ends.

14 Claims, 12 Drawing Sheets

DOUBLE ACTING, DUAL PIVOT THORACOSCOPIC SURGICAL LUNG CLAMPS

This is a continuation-in-part of U.S. Ser. No. 07/680,392 filed Apr. 4, 1991 now U.S. Pat. No. 5,192,298, which is hereby incorporated by reference herein in its entirety. This application is related to U.S. Pat. No. 5,171,258 which is hereby incorporated by reference herein in its entirety.

BACKGROUND OF THE INVENTION

The present invention broadly relates to endoscopic surgical instruments. More particularly, the invention relates to disposable endoscopic lung clamps which are usefu in thoracoscopic procedures.

Endoscopy procedures such as thoracoscopy and laparoscopy have recently become widely practiced surgical procedures. A laparoscopy procedure typically involves incising through the navel and through the abdominal wall for viewing and/or operating on the ovaries, uterus, gall bladder, bowels, appendix, etc. More recently, incisions and insertion of trocar tubes have been made in different areas of the abdomen and even in the chest cavity (thoracoscopy). Typically, trocars are utilized for creating the incisions. Trocar tubes are left in place in the abdominal or thoracic wall so that the endoscopic surgical tools may be inserted through the tube. A camera or magnifying lens is often inserted through the largest diameter trocar tube (e.g. 10 mm diameter), while a cutter, dissector, or other surgical instrument is inserted through a similarly sized or smaller diameter trocar tube (e.g. 5 mm diameter) for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut or stitched with another surgical instrument; all under view of the surgeon via the camera in place in the navel trocar tube.

Previous to the present invention, endoscopic tools have utilized connecting mechanisms for imparting pivotal motion to the manipulating members of the end effectors. These tools, however, have utilized either single pivot mechanisms specifically designed to avoid protrusions outside of the outline of the endoscopic tool so as to avoid any inadvertent contact with tissue of a patient, or double pivot mechanisms such as disclosed in U.S. Pat. No. 3,895,636 to Schmidt where the manipulating members are directly actuated by the axial movement of a common reciprocating member. While such tools have functioned adequately for many of their intended purposes, these endoscopic tools have not enabled the desired amount of gripping or cutting force important in the manipulation of large vessels or organs, such as might be required in procedures involving, e.g., intestinal organs. Also, previous to the present invention, thoracoscopic lung clamps having end effectors of two inches or more in length, and cut-outs in the distal portion of the end effectors were not available to the art.

SUMMARY OF THE INVENTION

It is therefore an object of the invention to provide disposable thoracoscopic surgical instruments particularly suited for surgical procedures involving larger organs, such as lungs.

Another object of the invention is to provide disposable endoscopic surgical instruments of improved design with high leverage end effectors and with connecting mechanisms of very small cross section which do not protrude outside of the envelope of the instrument.

It is a further object of the invention to provide a disposable endoscopic lung clamp surgical instrument which utilizes an improved linkage system which enables increased leverage to be applied to the manipulation members of the end effector of the instrument.

In accord with the objects of the invention, a disposable thoracoscopic lung clamp generally includes: a tube; a push rod which extends through the tube; an actuating means engaging the tube and the push rod for imparting reciprocal axial motion to the push rod; end effector lung clamp means coupled at their proximal ends to the push rod by connecting means which are also coupled to the push rod; a clevis coupled to the tube at its proximal end and to the end effector means at its distal end; and posts coupled to the clevis and extending through the lung clamp end effector means such that the lung clamp end effector means rotate thereabout, with the posts being transverse and displaced relative to the longitudinal axis of the tube, wherein axial movement of the push rod effects movement of the lung clamp end effector means in a plane parallel to the longitudinal axis of the push rod.

Plastic shrink wrap is preferably utilized to electrically insulate the disposable instrument and extends over the aluminum tube and over at least an adjacent portion of the clevis. The tube is preferably made of aluminum, the push rod is preferably made of stainless steel, the clevis is preferably made of a high-strength aluminum alloy, the actuating means is preferably made of plastic and aluminum, and the end effector means is preferably made of stainless steel or investment cast bronze.

The clevis of the invention is preferably a separately formed clevis having a knurled rod-like proximal end for mating with the end of the aluminum tube, and a U-shaped distal portion for supporting the posts which around which the end effector means rotate. A first post in the distal portion of the clevis is perpendicular to the legs of the U-shaped distal portion and transverse to the longitudinal axis of the aluminum tube and the push rod. The post is displaced from the longitudinal axis and arranged to extend through hole(s) in the manipulating members of the end effector means. The second transverse post is provided adjacent to and opposite the first post on the opposite side of the longitudinal axis. In this manner, the blades or prongs of the manipulating members of the end effector means are held by respective axially offset pivot posts and can respectively rotate around the posts. A high degree of leverage is thereby developed in the manipulation members of the end effector.

The end effector lung clamp means of the invention preferably is a double acting mechanism, with the clamp elements being between two and three inches in length from their pivot points to their distal ends, and including extended cut-out portions of between ⅛ and ⅜ inch long at their distal ends. The opposing clamping surfaces of the clamping elements have grooves running transverse the longitudinal axis of the clamping elements. Each manipulation member of the end effector is preferably arranged with a hole to accept a post of the clevis so that each manipulation member rotates around a different post.

According to one aspect of the invention, the push rod is flattened on its distal end, and the linkage means which couple the push rod and the end effectors both extend through a hole in the flattened end of the push rod as well as through other holes in the proximal ends of the end effectors. Because the outer tube is positioned at a fixed distance from the rotation hole in the end effector (due to the clevis), when the push rod is moved axially relative to the tube, the end effectors cannot move axially. However, because the push rod is also a fixed distance away from holes in the proximal ends of the end effectors (due to the connecting means), movement of the push rod relative to the tube causes rotation of the end effectors in a plane In other words, movement of the push rod relative to the tube causes the holes through the end effectors through which the linkage members extend to rotate along arcs centered at the rotation holes in the end effectors through which the transverse posts extend. Movement in this manner typically effects a grasping action.

A better understanding of the disposable endoscopic lung clamp instruments of the invention, and additional advantages and objects of the invention will become apparent to those skilled in the art upon reference to the detailed description and accompanying drawings.

BRIEF DESCRIPTION OF THE DRAWINGS

FIG. 1 is a side elevation view, partly in section, of a disposable surgical instrument prior to insertion into a trocar tube, and, in partial phantom format, after insertion into a trocar tube;

FIG. 1A-1 is a cross-section through the instrument of FIG. 1 at the indicated location of FIG. 1;

FIG. 2b is a cross-section View of the device of FIG. 2a;

FIG. 3b is a rear elevation view of the device of FIG. 3a;

FIGS. 5A, 5A-1, 5B, and 5B-1 are views of elements of the device of FIG. 5;

DETAILED DESCRIPTION OF THE PREFERRED EMBODIMENT

Figures 1, 1A:
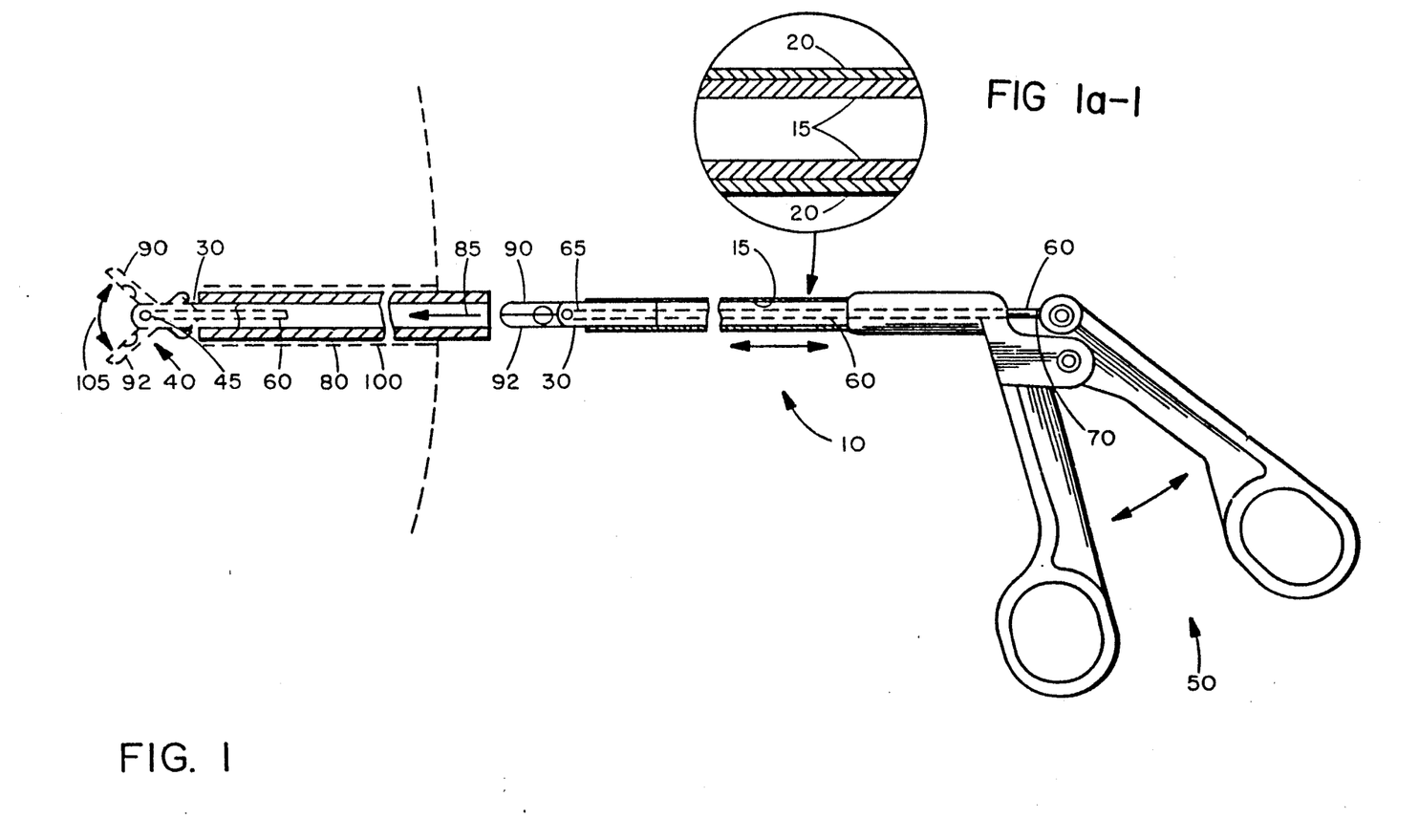

With reference to FIGS. 1 and 1A-1, disposable surgical instrument is indicated at 10. The disposable surgical instrument 10 includes an aluminum tube 15 surrounded by a peripheral insulating shrink wrap layer of plastic 20, a clevis means 30, end effectors 40, actuating means 50, and a push rod 60. The clevis means 30 is preferably a separately formed aluminum piece which fixedly engages aluminum tube 15 as described in more detail hereinafter. The clevis 30 also engages the manipulating members 90, 92 of the end effector 40 which are respectively pivotally engaged to clevis 30 at pivot pins 45, 47 as hereinafter more particularly described. End effector 40 may be formed of investment cast bronze as disclosed in copending U.S. Ser. No. 07/521,766 which was previously incorporated by reference herein, or can be formed of investment cast stainless steel, other metals, or plastic as desired. The push rod 60, which is also preferably formed of stainless steel, is engaged at its distal end 65 to the end effector 40, as hereinafter more fully described, and is connected at 70, at its proximal end, to a manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the surgical instrument 10 is inserted with the manipulation members, e.g. blades, clamps, or graspers 90, 92 of the end effector 40, in the closed position, into trocar tube 80, as indicated at the arrow 85 of FIG. 1. The distal portion of the instrument 10 passes through the trocar tube 80 into body incision 100. Upon the distal portion of the surgical instrument 10 exiting the trocar tube 80, the manipulating members, e.g. clamp elements 90, 92 can be opened and closed as indicated at 105 by reciprocal motion of push rod 60 which results from operation of the manual actuating means 50. As is discussed more fully hereinafter, the clevis effectively helps translate the reciprocal motion of the push rod 60 into the end effector means action indicated at 105.

Figure 2A:
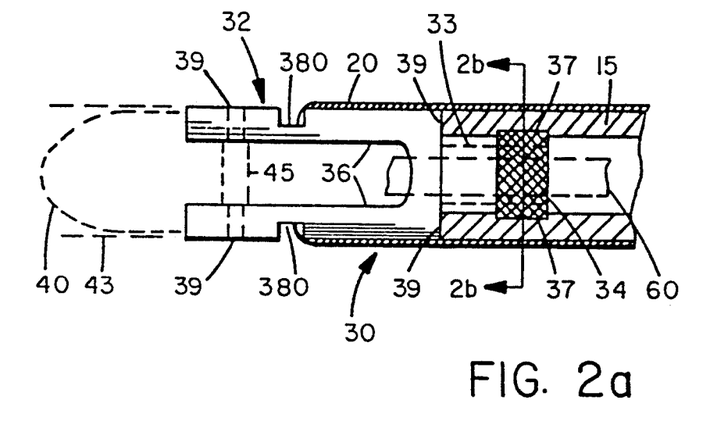
FIG. 2a is a side elevation view, partly in section, of the clevis of the invention in conjunction with the distal end of the tube and shrink wrap of the invention.
Figure 2B:
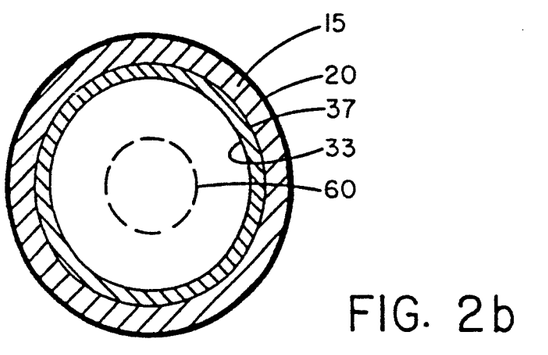
Figure 2C:
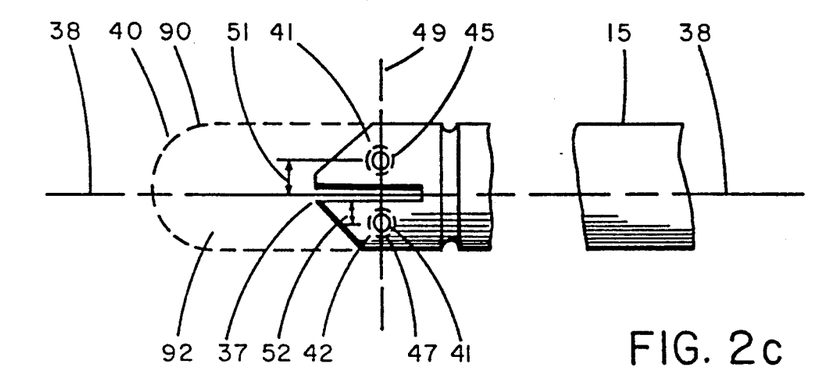
FIG. 2c shows the device of FIG. 2a rotated by 90°.
Figure 2D:
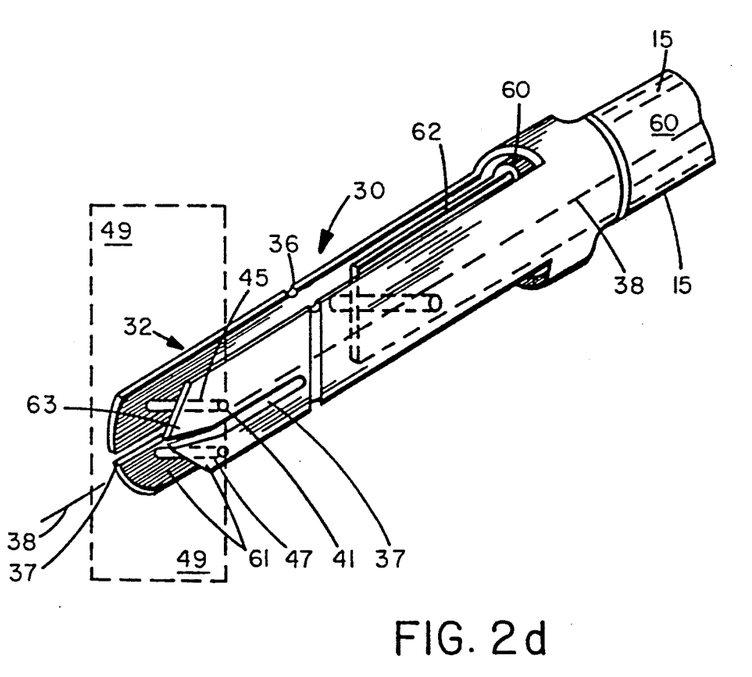
FIG. 2d is a perspective view of the clevis element shown in FIG. 2a, along with the transverse posts.

Turning to FIGS. 2a, 2b, 2c and the perspective view of FIG. 2d, a preferred configuration of the clevis 30 of the present invention is seen. The clevis has a knurled rod-like proximal portion 34 for mating with the end of the aluminum tube 15, and a post-supporting U-shaped distal portion 32 for holding the end effector means. The proximal portion 34 of the clevis is preferably hollow, as indicated at 33, to permit the push rod 60, with its flattened terminal portion 62 to extend therethrough. The distal portion 32 of the clevis 30 is provided with a first post or pivot pin 45, a second post or pivot pin 47, and legs 36, which have slots 137 to increase their flexibility and to allow independent adjustment of the two pivot posts 45 and 47. The posts 45, 47 are generally perpendicular, i.e. transverse, to the legs 36 of the clevis and are arranged to extend respectively through holes 41, 42 in the manipulation members 90, 92 of end effector means 40. In this manner, the blades, clamps, or prongs 90, 92 of the end effector means 40 are held by, but can rotate around the posts 45, 47 (i.e. they are rotatably respectively engaged therewith) which are symmetrically disposed about longitudinal axis 38 and which are in a common plane which is transverse to longitudinal axis 38. Push rod 60, tube 15 and clevis 30 all have substantially the same common longitudinal axis 38. Posts 45, 47 are transverse to and displaced from axis 38 on opposite sides thereof as indicated at 51, 52 in FIG. 2c.

As seen in FIG. 2a, a recess or notch 380 is provided which extends across each leg 36 of the clevis 30. Consequently, a peripherally applied electrically insulating plastic wrap 20 can be end-cut at recess 380 and a smooth transition from the end effector means 40 via the clevis 30 to tube 15 can be achieved. Even if slight outward flaring of wrap 20 occurs at the end-cut, as is common, this flaring can be tolerated as it will be within the envelope of the normal outer instrument surface indicated at 43.

Clevis 30 is preferably made from a high strength aluminum base alloy (e.g. 2024 alloy of Alcoa) which is preferably harder than the aluminum base alloy (e.,g. 6061 or 6063 alloys of Alcoa) from which tube 15 is fabricated. The post elements 45, 47 portion of the clevis 30 may be made out of a high strength aluminum alloy or, for added strength, out of a stainless steel screw or nail. In assembly of the surgical instrument 10, serrated or knurled portion 34 of clevis 10 is fit snugly into tube 15 such that the walls of tube 15 abut the peripheral shoulder 39 of clevis 30, with the outer surface of tube 15 and the adjacent outer surface of clevis 30 having essentially the same diameter. Mechanical pressure is then applied to tube 15 peripherally at the location of knurled portion 34, thereby crimping the end portion of tube 15 onto the knurled portion 34. Mechanical pressure causes the projections of the knurls to bite into and firmly engage tube 15 as indicated at 37 due to the higher hardness of the clevis material. Alternately, the clevis may be pressed into the tube. Once the clevis 30 and tube 15 have been properly joined, the plastic shrink wrap 20 can be applied over the tube 15 and an adjacent portion of the clevis 30 and end-cut at recess 380. Alternately, the plastic shrink wrap may be applied after the end effectors are attached to the instrument by the posts as hereinafter described.

Figure 3A:
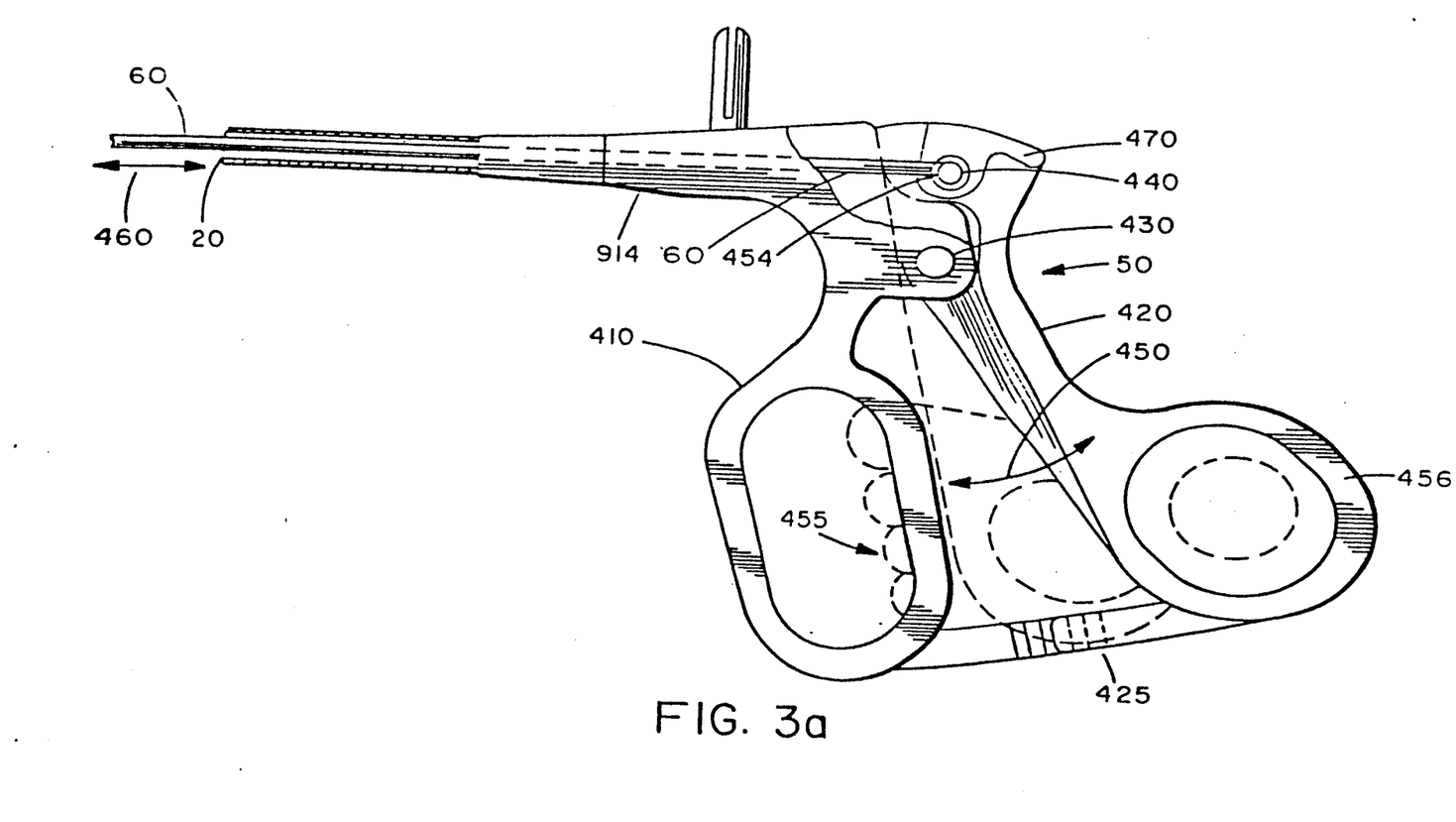
FIG. 3a is a partially broken-away side elevation view of the actuating handle of the disposable surgical instrument of the invention.
Figure 3B:
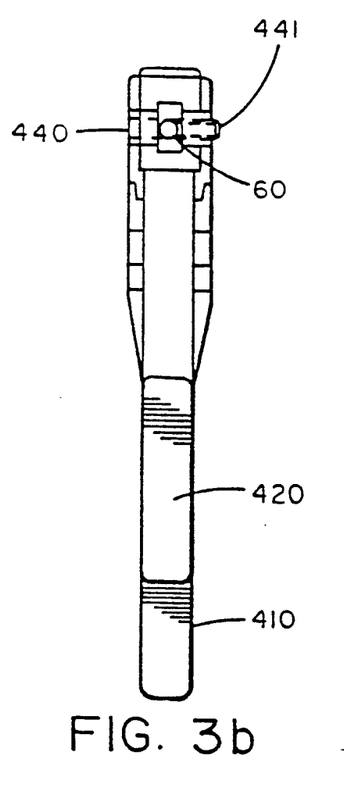

With reference to FIGS. 3a and 3b, manually operable actuating means are indicated at 50 which includes an electrically insulating housing 914 having a fixed handle portion 410 integral therewith and a lever portion 420 pivotally engaged to housing 914 at pivot pin 430. Push rod 60 passes through aluminum tube 15 (covered by shrink wrap 20) and engages cross pin 440 at 454; set screw 441 being used to extend into cross pin 440 and set push rod 60 in the cross pin 440. The cross pin 440 is fixedly positioned in lever member 420. Upon pivotal motion of lever arm 420, as indicated at 450, using a conventional hand grip as indicated at 455 to apply pressure to extended handle element 456 of lever member 420, push rod 60 will move linearly as indicated at 460 to actuate an end-effector (not shown in FIG. 3a) coupled thereto as hereinabove described. A customary, state-of-the art ratchet type holding mechanism is shown at 425 for locking lever portion 420 relative to handle 410.

Figure 5:
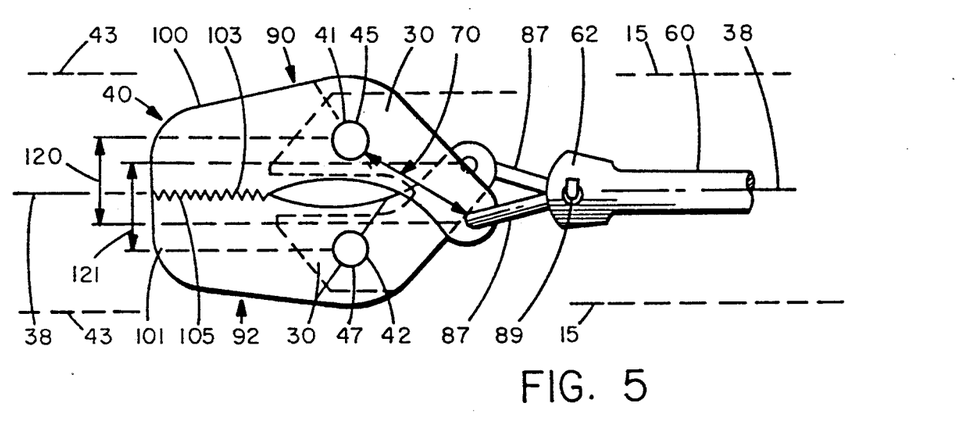
FIG. 5 is a side elevation view of the dual pivot instrument of the present in a closed position.

With reference to FIGS. 5, 5(A), 5(A)-1, 5(B), 5(B)-1, and 5(C), a preferred dual pivot end effector 40, in the form of a grasper, is shown. End effector 40 comprises manipulation members 90, 92 which are separately shown in FIGS. 5(A) and 5(A)-1, 5(B), and 5(B)-1. For the end effector 40, the manipulation members 90, 92 are essentially identical, with one being inverted 180° with respect to the other when arranged for operation in an instrument as shown in FIG. 5. Manipulation members 90, 92 each have an extended forward edged portion 100, 101, with opposed edges 103, 105 for grasping, cutting and the like. Base members 107, 109, integral with forward edged members are obliquely angled inwardly forward their associated edges 103, 105 as shown at 111, 113. Base member 107, 109 function as lever arms and are provided with through holes 41, 42 for respectively engaging pivot posts 45, 47 of clevis 30 which is shown in "phantom" in FIG. 5.

Figure 7:
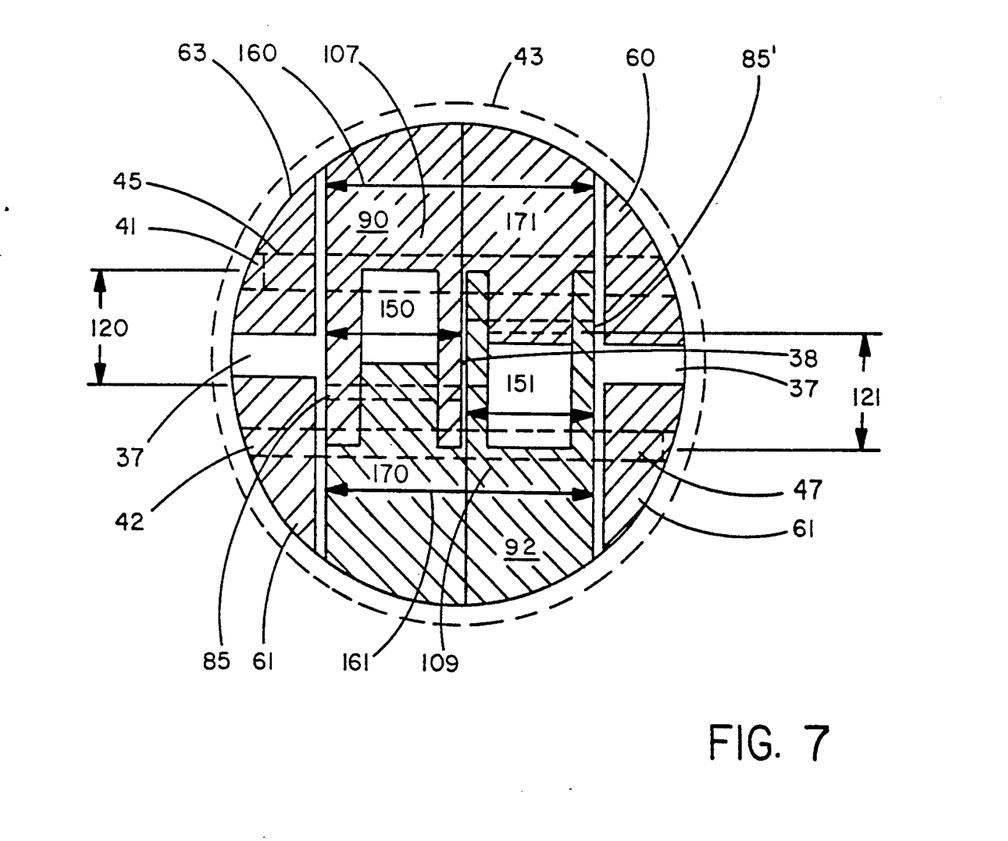
FIG. 7 is a rear sectional elevation view of the device of FIG. 6 along 7—7.
Figures 8, 9:
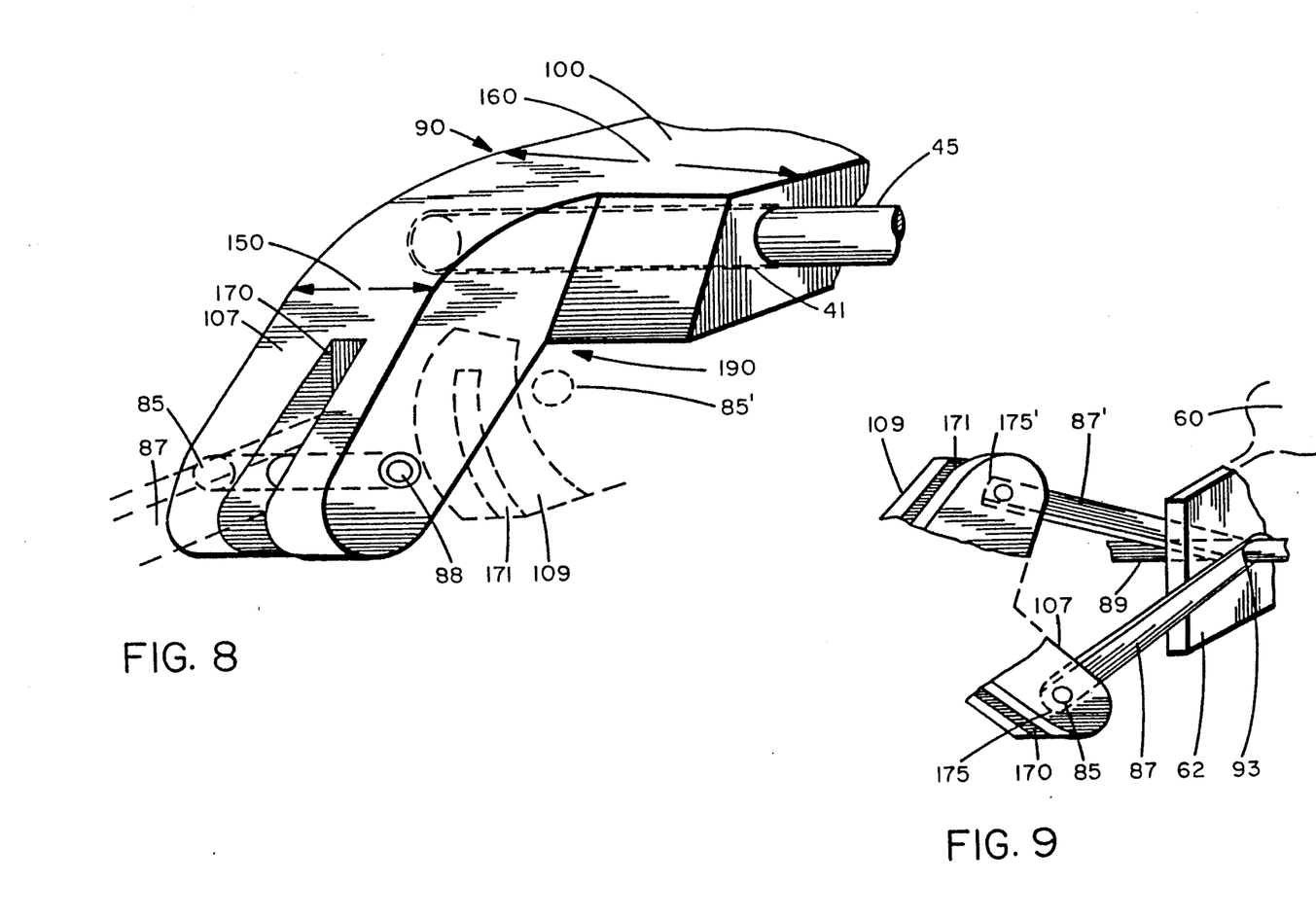
FIG. 8 is a partial perspective view of a manipulation member of an end effector.
FIG. 9 is a partial perspective view of the linkage shown in FIG. 5.

Posts 45, 47 are positioned transverse to longitudinal axis 38 of clevis 30, rod 60 and tube 15 as hereinabove described, and posts 45, 47 are each displaced radially outward and away from longitudinal axis 38 by the distances shown at 120, 121 in FIG. 5 and FIG. 7. The offset distance's 120, 121 can be as large or larger than one-half of the diameter 43 of the instrument, and the longer the distances 120, 121, the greater the leverage that can be obtained and the greater the force that can be applied by the manipulation members 90, 92 end effector 40 to large organs and anatomic structures. Displaced posts 45, 47 of the device of FIG. 5 are suitably stainless steel screws which engage holes 41, 42 and are positioned directly opposite to each other in a common transverse plane on opposite sides of the longitudinal axis 38 and are suitably respectively engaged at about the midpoint of clevis quadrant segments 61, 63 shown in FIG. 2d and FIG. 7 which are separated by axial slots 37.

Figures 5A, 5A:
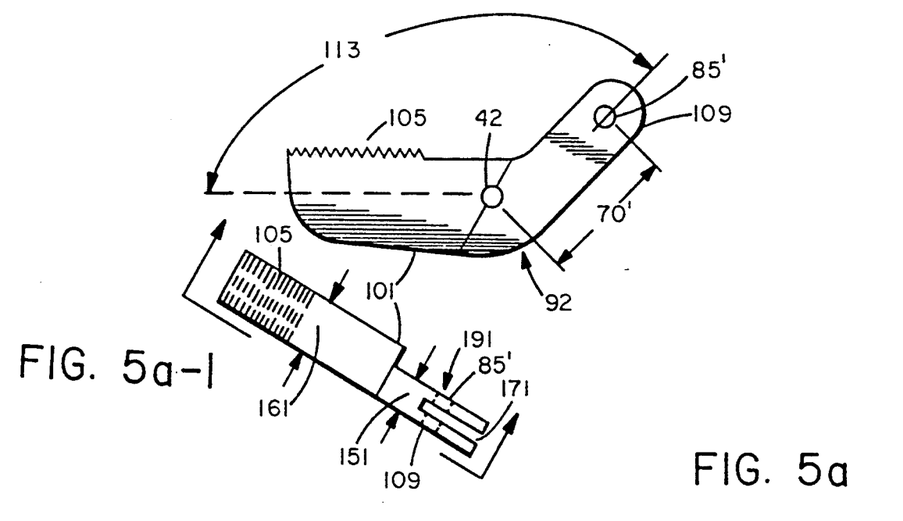
Figures 5B, 5B:
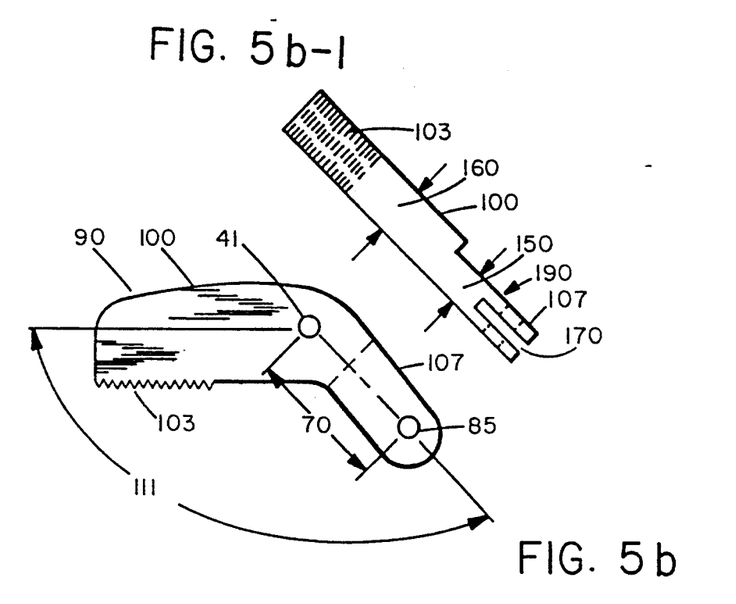
Figure 5C:
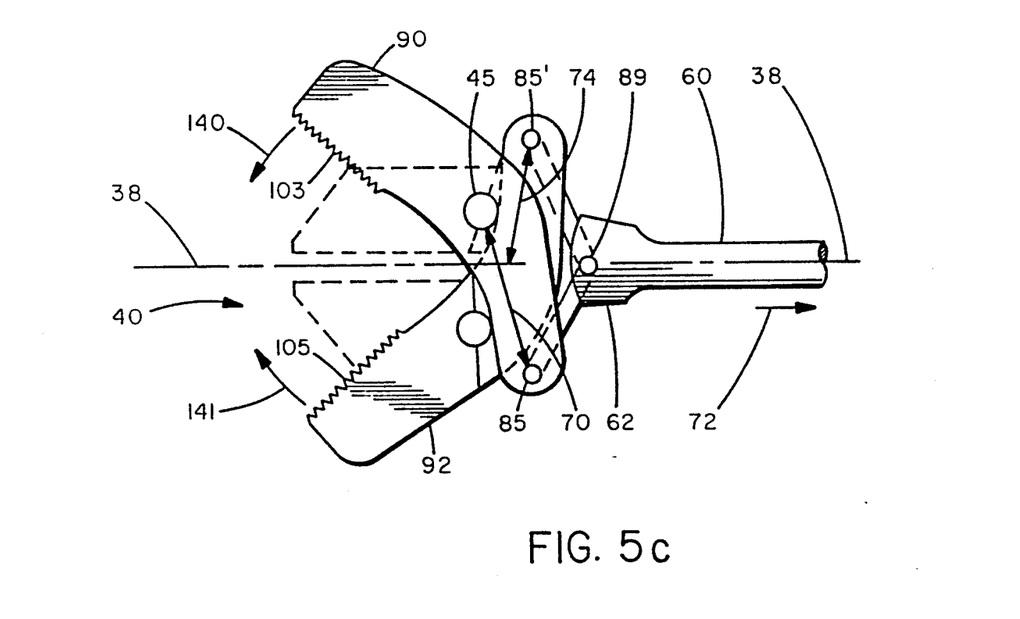
FIG. 5c is a side elevation view of the device of FIG. 5 in an open position.
Figure 6:
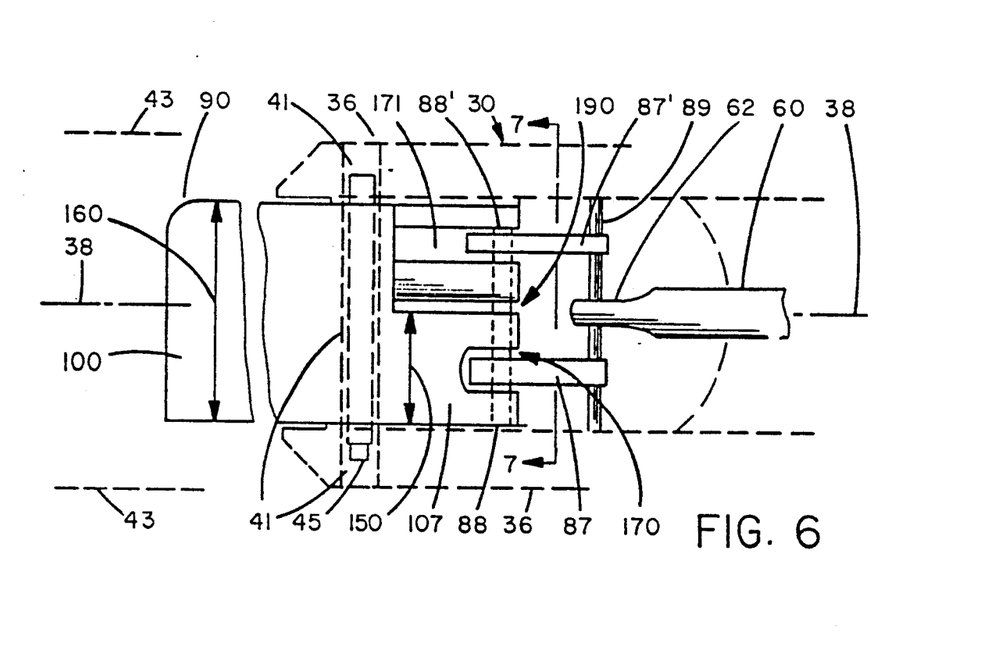
FIG. 6 is a plan view of the device of FIG. 5.

The provision of two separate axially displaced pivot posts 45, 47 for the respective manipulation members 90, 92 in accordance with the present invention establishes a lever arm indicated at 70 in the end effector "open" position of FIG. 5c when push rod 60 is moved in the axial direction indicated at 72. Lever arm 70, for manipulation member 90, is the distance from pivot 45 to the through hole 85 in member 90 which pivotally engages linkage means 87. Linkage means is suitably a thin metal bar e.g. stainless steel, to which flattened portion 62 of push rod 60 is pivotally engaged. Engagement is obtained by transverse pivot rod 89 which passes through hole 93 of metal linkage bar 87.

Figure 4:
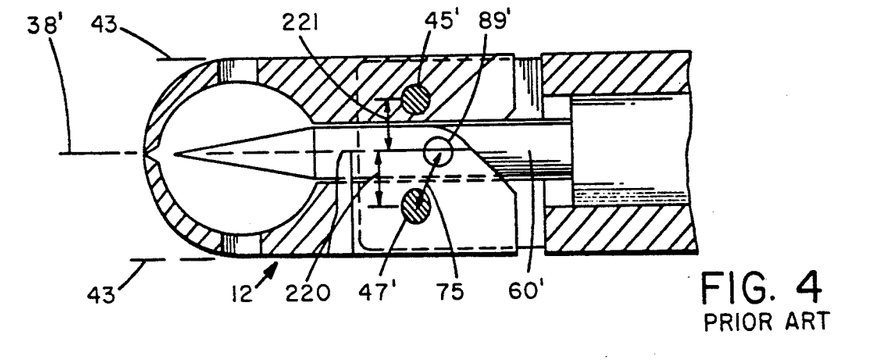
FIG. 4 is a side elevation view of a prior art instrument.

A comparison between prior art devices such as seen in FIG. 4, and the device of the invention shows that the prior art devices such as device 12 of FIG. 4 have axial offsets 220, 221 which are less than the offsets 120, 121 of the device of FIG. 5 of this invention. Comparison also shows that the lever arm 70 of the device of FIG. 5 is, and can always be greater in length than the lever arm 75 of the prior art axially in-line arrangement of FIG. 4, e.g. by at least the incremental distance shown at 74 in FIG. 5(C). This distance 74 extends from the longitudinal axis 38 to the hole 85 in the base portion of the manipulation member 90.

The offset distance 220 of the prior art device of FIG. 4 is limited to a distance of less than one half of the instrument outline 34. This restriction results in devices with only limited leverage being available. Limited leverage is disadvantageous, especially in manipulating large organs and anatomic parts. On the other hand, the offset distances 120, 121 in the dual pivot device of this invention shown in FIG. 5 can be as much as one half the diameter of the outline and even more, while avoiding protrusion of the linking mechanism members 87, 87' outside of the outline 43 of the instrument.

The above described lever arm relationship of manipulation member 90 also applies to manipulation member 92 as indicated at 70' in FIG. 5a. With the above described dual pivot post configuration, movement of push rod 60 in the direction 72 shown in FIG. 5c causes transverse push rod pivot 89 to move in the same direction, and results in rotation of manipulation members 90, 92 in the directions indicated at 140, 141 in FIG. 5c. Due to the extended lever arms 70, 70' hereinbefore described an increased leverage is developed which results in increased pressure on an organ or vessel positioned adjacently in contact with edges 103, 105. This increased pressure through the utilization of two pivot posts is attainable without any increased protrusion of the mechanism outside of the outline 43 of the surgical instrument. This is due in part to the configuration of the manipulsation members 90, 92 whereby the base members 107, 109 thereof have a width 150, 151 which is less than the width 160, 161 of the forward edged portions 100, 101 as shown in FIGS. 5a, 5b, the top plan view of FIG. 6, the rear sectional elevation view of FIG. 7 and the partial perspective view of FIG. 8. In the embodiment shown, the width of the members 107, 109 is slightly less than one-half the width of the forward edged members 100, 101. As also shown in FIGS. 5(A)-1, 5(B)-1, 6, 7 and 8, the base members 107, 109 have respective slots 170, 171 which receive the end portions 175, 175' of link members 87, 87' which are remote from pivot 89 of the flattened portion 62 of push-rod 60. The end portions 175, 175' of link members 87, 87' are pivotally engaged at holes 85, 85' by pins 88, 88'. Since the widths of base members 107, 109 are less than the full width of the forward edged portions 100, 101, recesses 190, 191 are established laterally adjacent and inward from the base members 107, 109. These recesses 190, 191 respectively receive base members 107, 109 of manipulation members 90, 92 in the course of their pivotal movement during opening and closing of the end effector 40, thus eliminating any interference due to the utilization of dual transverse pivot posts 47, 47' which are aligned in a plane transverse to longitudinal axis 38.

Figure 10A:
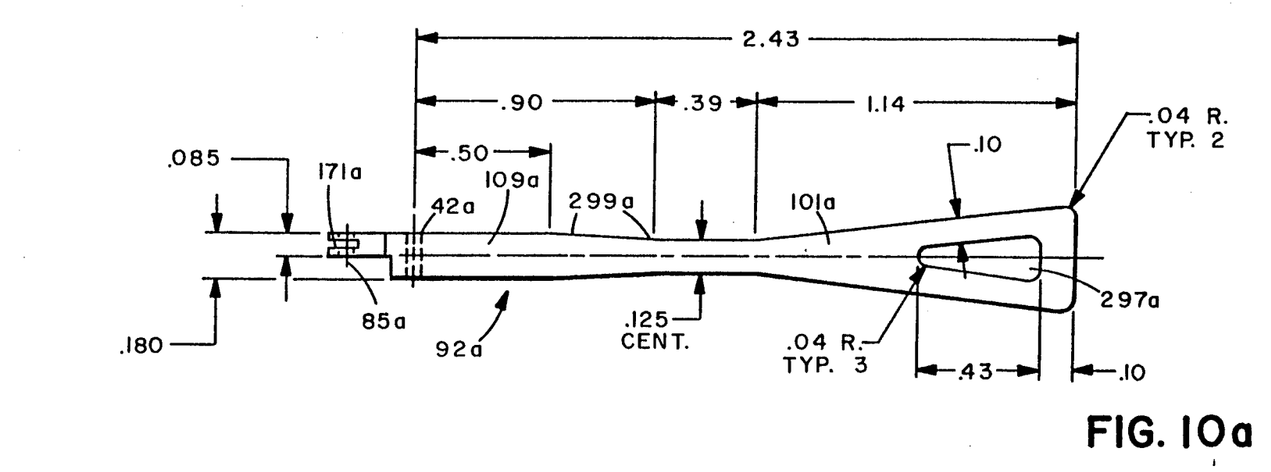
FIGS. 10a and 10b are top plan and side elevational views of a first preferred embodiment of the lung clamp end effector elements of the invention.
Figure 10B:
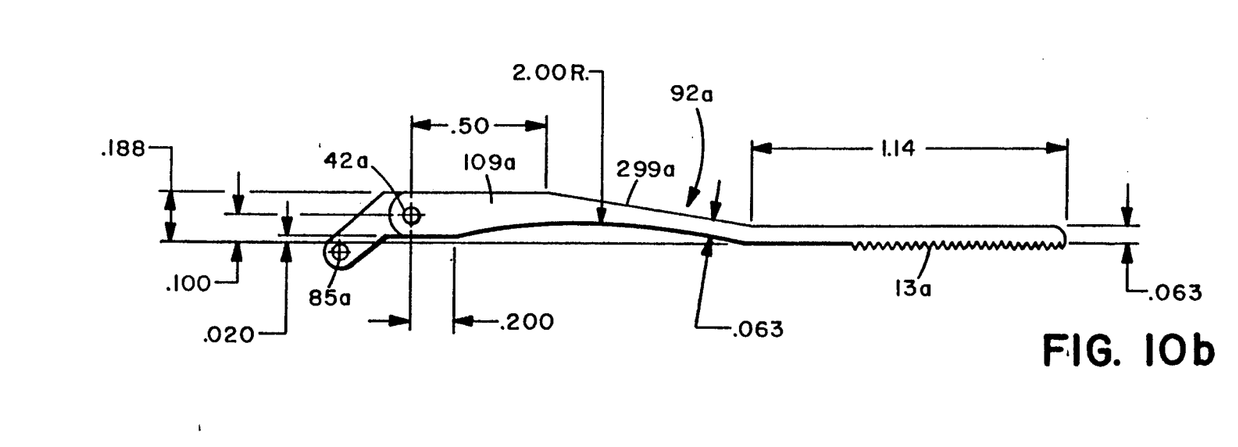

Turning to FIGS. 10a and 10b, a Duval-type lung clamp end effector 92a is seen, with representative dimensions (in inches unless otherwise noted) indicated. The lung clamp end effector has a base portion 109a with through-hole 42a for a pivot rod of the clevis and through-hole 85a for a pin which connects a connecting means to the actuating rod, an intermediate portion 299a, and the distal portion 101a. Base portion is arranged precisely as shown in FIGS. 5(A)-1, 5(B)-1, 6, 7, 8, and 9, except that as seen in FIG. 10b, the thickness tapers slightly so that the base extends slightly away from the longitudinal axis defined by the clamping face 13a of the distal end of the clamp 92a. As seen in FIGS. 10a and 10b, the intermediate portion 299a tapers both in its thickness and width, and extends back down toward the longitudinal axis. The distal portion 101a, as seen in FIG. 10b remains about the thickness 0.063 inches) as the intermediate portion. However, the distal portion 101a flares outwardly as it extends away from the intermediate portion 299a until it reaches approximately 10 mm in width. The distal portion 101a includes a cut-out 297a of a generally rounded triangular form, with each leg of the distal portion 101a surrounding the cut-out 297a being of about 0.10 inch in width. The clamping face 13a of at least a portion of distal portion 101a is grooved with the grooves running transverse the longitudinal axis of the clamp member. The total length of the Duval-type lung clamp end effector 92a from the pivot point 42a to the distal end of distal portion 101a is preferably about 2.43 inches, with the length of the base portion from the pivot point to its distal end being about 0.5 inches; the length of intermediate portion being about 0.79 inches; and the length of distal portion being about 1.14 inches. Because the clamp member 92b is comparatively long for a 10 mm surgical instrument, the dual pivot mechanism discussed above with reference to FIGS. 5-9 is particularly effective in providing the desired clamping action.

Figure 11A:
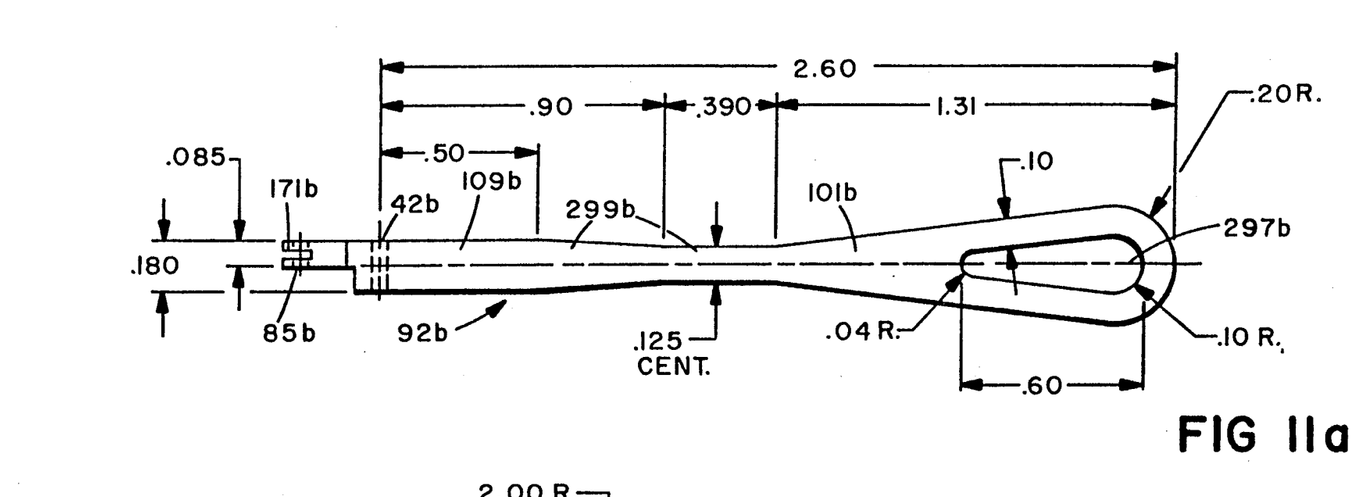
FIGS. 11a and 11b are top plan and side elevational views of a second preferred embodiment of the lung clamp end effector elements of the invention.
Figure 11B:
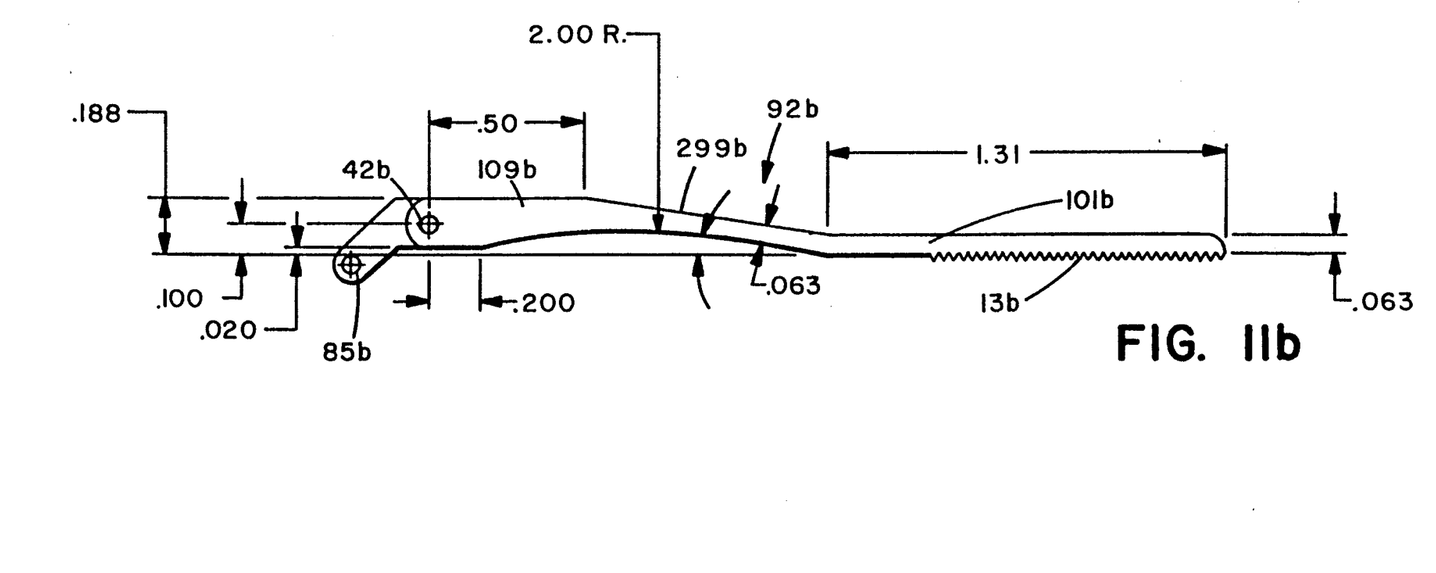

Turning to FIGS. 11a and 11b, a second lung clamp end effector 92b is seen, with representative dimensions (in inches unless otherwise noted) indicated. The second lung clamp end effector 92b has a base portion 109b with through-hole 42b for a pivot rod of the clevis and through hole 85b for a pin which connects a connecting means to the actuating rod, an intermediate portion 299b, and the distal portion 101b. The base portion 109b is arranged precisely as shown in FIGS. 10a and 10b, with exactly the same dimensions. Likewise, the intermediate portion 299b of lung clamp 92b is arranged precisely as shown in FIGS. 10a and 10b with exactly the same dimensions. The only difference between the lung clamp of FIGS. 11a and 11b and that of FIGS. 10a and 10b is the distal portion 101b. As seen in FIG. 10b, the distal portion 101b, remains about the thickness 0.063 inches) as the intermediate portion but flares outwardly as it extends away from the intermediate portion 299b until it reaches a width of about 10 mm. The distal portion 101b includes a cut-out 297b of a generally thin pear-shaped form, with the two straight legs and the semicircular leg of the distal portion 101b surrounding the cut-out 297b being of about 0.10 inch in width. The clamping face 13b of at least a portion of distal portion 101b is grooved with the grooves running transverse the longitudinal axis of the clamp member. The total length of the lung clamp end effector 92b from the pivot point 42b to the distal end of distal portion 101b is preferably about 2.60 inches, with the length of the base portion from the pivot point to its distal end being about 0.5 inches; the length of intermediate portion being about 0.79 inches; and the length of distal portion being about 1.31 inches. Because the clamp member 91a is comparatively long for a 10 mm surgical instrument, the dual pivot mechanism discussed above with reference to FIGS. 5-9 is particularly effective in providing the desired clamping action.

There has been described and illustrated herein a double acting, dual pivot thoracoscopic lung clamp instrument. While particular embodiments of the invention have been described, it is not intended that the invention be limited exactly thereto, as it is intended that the invention be as broad in scope as the art will permit. Thus, while exact dimensions for the lung clamp end effector elements have been provided, it will be appreciated that other dimensions can be utilized, provided that the lung clamp end effector elements are generally long (i.e., greater than two inches from the point of rotation to the distal end), have widening distal portions (i.e., which widen to about 10 mm) which include cut-outs therein, and have a grooved clamping surface. Also, while preferred mechanisms for causing the lung clamp end effector elements to pivot are set forth, it will be appreciated that other arrangements, such as set forth in previously incorporated U.S. Ser. No. 07/680,392 can be utilized. Therefore, it will be apparent to those skilled in the art that other changes and modifications may be made to the invention as described in the specification without departing from the spirit and scope of the invention as so claimed.

What is claimed is:

1. In a lung clamp surgical instrument comprising an outer tube having a first longitudinal axis, a clevis means for coupling to said outer tube, first and second clamp end effectors each having a base portion having a first through-hole transverse said longitudinal axis for pivotally engaging said clevis means, and actuation means coupled to said clamp end effectors for effecting rotational movement of said clamp end effectors around said clevis means, an improvement comprising:

in said clamp end effectors, each said end effector including said base portion, an intermediate portion, and a distal portion having proximal and distal ends, each distal portion having a first width at its proximal end defined by a horizontal axis substantially parallel to said first through-hole and increasing in width to no more than approximately 10 mm as it extends distally and having a cut-out increasing in width as said distal portion extends distally, each said clamp end effector being at least two inches long from its respective first through-hole to its respective said distal end, with at least a part of said distal poriton of each said clamp end effector having a grooved clamping surface, and wherein in a first position, said grooved clamping surface of the distal portion of one lung clamp end effector is touching the grooved clamping surface of the distal portion of the other lung clam end effector, and wherein each said base portion tapers in thickness from a larger thicknesses to a smaller thickness as it extends distally, and each intermediate portion is thinner than each bs portion and narrows in width as it extends away from said base portion.

2. In a lung clamp surgical instrument according to claim 1, wherein:

as each base portion tapers in thickness it extends away from a second longitudinal axis parallel to said longitudinal axis of said outer tube, and each said intermediate portion extends from said base portion away from said second longitudinal axis back to said second longitudinal axis.

3. In a lung clamp surgical instrument according to claim 2, wherein:

said cut-out si generally triangular-shaped with rounded corners.

4. In a lung clamp surgical instrument according to claim 2, wherein:

said cut-out has a first rounded end of a first diameter, a second rounded end of a second diameter, said second diameter being larger than said first diameter, and skewed sides extending from said first rounded end to said second rounded end.

5. In a lung clamp surgical instrument according to claim 1, wherein:

said cut-out has a first rounded end of a first diameter, a second rounded end of a second diameter, said second diameter being larger than said first diameter, and skewed sides extending from said first rounded end to said second rounded end.

6. In a lung clamp surgical instrument according to claim 5, wherein:

said distal portion after increasing in width to approximately 10 mm is rounded at its distal end as it extends around said second rounded end of said cut-out.

7. In a lung clamp surgical instrument according to claim 1, wherein:

said cut-out is generally triangular-shaped with rounded corners.

8. A thoracoscopic lung clamp apparatus for the manipulation of lung tissue, comprising:

a) a longitudinally extending push rod having a first end portion and a second end portion remote from said first end portion;

b) a longitudinally extending tube surrounding said push rod along most of its length between said first and second end portions thereof, said longitudinally extending tube having a first longitudinal axis;

c) actuating means engaging said push rod at said second end thereof for imparting reciprocal axial longitudinal motion to said push rod relative to said tube;

d) a clevis means for coupling to said tube member adjacent said first end of said push rod;

e) at least one post means for engaging said clevis means, with said post means transverse to said first longitudinal axis said post means being spaced from said first end of said push rod in a direction opposite to the second end of said push rod;

f) first and second pivotally mounted elongate opposed lung clamp members, each clamp member including a base portion, an intermediate portion, and a distal portion having proximal and distal ends, each base portion having a first through-hole pivotally engaging a said post means, each distal portion having a first width at its proximal end defined by a horizontal axis substantially parallel said at least one post means and increasing in width to no more than approximately 10 mm as it extends distally and having a cut-out increasing in width as said distal portion extends distally, each said lung clamp member being at least two inches long from its respective first through-hole to its respective distal end, with said distal end having a grooved clamping surface, wherein in a first position, said grooved clamping surface of the distal portion of one lung clamp member is touching the grooved clamping surface of the distal portion of the other lung clamp member, and wherein each said base portion tapers in thickness from a larger thickness to a smaller thicknesses as it extends distally, and each intermediate portion is thinner than each base portion and narrows in width as it extends away from said base portion;

g) first and second connecting means for respectively coupling said first and second pivotally mounted elongate opposed clamp members to said push rod.

9. A thoracoscopic lung clamp apparatus according to claim 8, wherein:

as each base portion tapers in thickness it extends away from a second longitudinal axis parallel to said first longitudinal axis, and each said intermediate portion extends from said base portion away from said second longitudinal axis back to said second longitudinal axis.

10. A thoracoscopic lung clamp apparatus according to claim 9, wherein:

said cut-out is generally triangular-shaped with rounded corners.

11. A thoracoscopic lung clamp apparatus according to claim 9, wherein:

said cut-out has a first rounded end of a first diameter, a second rounded end of a second diameter, said second diameter being larger than said first diameter, and skewed sides extending from said first rounded end to said second rounded end.

12. A thoracoscopic lung clamp apparatus according to claim 11, wherein:

said distal portion after increasing in width to approximately 10 mm is rounded at its distal end as it extends around said second rounded end of said cut-out.

13. A thoracoscopic lung clamp apparatus according to claim 8, wherein: said cut-out is generally triangular-shaped with rounded corners.

14. A thoracoscopic lung clamp apparatus according to claim 8, wherein:

said cut-out has a first rounded end of a first diameter, a second rounded end of a second diameter, said second diameter being larger than said first diameter, and skewed sides extending from said first rounded end to said second rounded end.

* * * * *